US00PP22186P2

(12) United States Plant Patent
Armitage et al.

(10) Patent No.: US PP22,186 P2
(45) Date of Patent: Oct. 4, 2011

(54) ***GAILLARDIA* PLANT NAMED 'GEORGIA SUNSET'**

(50) Latin Name: *Gaillardia×grandiflora*
Varietal Denomination: Georgia Sunset

(75) Inventors: Allan M. Armitage, Athens, GA (US); David A. Knauft, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/800,573

(22) Filed: May 18, 2010

(51) Int. Cl.
*A01H 5/00* (2006.01)

(52) U.S. Cl. ..... Plt./431

(58) Field of Classification Search ..... Plt./431
See application file for complete search history.

*Primary Examiner* — Annette Para

(74) *Attorney, Agent, or Firm* — Davis Wright Tremaine LLP

(57) ABSTRACT

The new variety 'Georgia Sunset' is provided. The new variety 'Georgia Sunset' generally has bright two-tone flowers, a large flower size, and persistent flowering throughout the growing season. The new variety 'Georgia Sunset' has brighter yellow flowers and a longer blooming period than similar cultivars of *Gaillardia* plants currently on the market. The new variety 'Georgia Sunset' flowers for at least four months during the growing season.

6 Drawing Sheets

Latin name of the genus and species of the plant claimed: 'Georgia Sunset' is a *Gaillardia* plant that is a hybrid of the genus and species *Gaillardia×grandiflora*.

Variety denomination: The new *Gaillardia* plant claimed is of the variety denominated 'Georgia Sunset'.

BACKGROUND OF THE INVENTION

The present invention relates to the discovery of a new and distinct cultivar of *Gaillardia* plant botanically known as a *Gaillardia×grandiflora* and herein referred to as 'Georgia Sunset', as herein described and illustrated.

The new *Gaillardia* plant variety 'Georgia Sunset' was selected in Watkinsville, Ga. in 2007. The new variety 'Georgia Sunset' generally has bright two-tone flowers, a large flower size, and persistent flowering throughout the growing season.

Pedigree and history: The new *Gaillardia* plant variety 'Georgia Sunset' was one of many seedlings selected in summer 2007 in Watkinsville, Ga. and originated from open pollination of *Gaillardia* plants in the University of Georgia Trial Gardens in Athens, Ga. The maternal plant is likely the *Gaillardia* plant 'Arizona Sun' (unpatented). Seeds from the open-pollinated *Gaillardia* plants were collected in fall 2006 and grown out in containers and in the field at Watkinsville, Ga. The resulting seedlings, of which the new variety 'Georgia Sunset' was one, were selected in summer 2007. The new *Gaillardia* plant variety 'Georgia Sunset' has been evaluated and tested in Watkinsville, Ga. and Athens, Ga. since 2007.

The new *Gaillardia* plant variety 'Georgia Sunset' has been shown to maintain its distinguishing characteristics through successive asexual propagations by, for example, rooted stem cuttings. Plants from stem cuttings have been directly planted in the ground.

SUMMARY OF THE INVENTION

The new *Gaillardia* plant variety 'Georgia Sunset' has not been observed under all possible environmental conditions.

The phenotype may vary somewhat with variations in environment and cultural practices such as temperature and light intensity without, however, any variance in genotype.

The following traits have been repeatedly observed in Watkinsville and Athens, Ga., and are determined to be the unique characteristics of the new *Gaillardia* plant variety 'Georgia Sunset':

1. Bright two-tone (orange and yellow) flowers;
2. Large flower size;
3. Persistent flowering for at least four months during the growing season;
4. Excellent landscape performance, illustrating hardiness in U.S. Department of Agriculture (USDA) Zone 7b and possibly perennial in other parts of the U.S.;
5. Vigorous habit The new variety 'Georgia Sunset' can be compared to the *Gaillardia* varieties 'Sunburst Burgundy' (unpatented) and 'Sunburst Scarlet Halo' (unpatented).

Comparison to 'Sunburst Burgundy'. The new variety 'Georgia Sunset' is in flower longer than 'Sunburst Scarlet Halo.'

Comparison to 'Sunburst Scarlet Halo'. The new variety 'Georgia Sunset' is more vigorous than 'Sunburst Scarlet Halo'. In addition, the new variety 'Georgia Sunset' is in flower longer than 'Sunburst Scarlet Halo.'

BRIEF DESCRIPTION OF THE FIGURES

The accompanying photographic illustration shows typical specimens in full color of the foliage and fruit of the new variety 'Georgia Sunset'. The colors are as nearly true as is reasonably possible in a color representation of this type.

BOTANICAL DESCRIPTION

Figure 1:
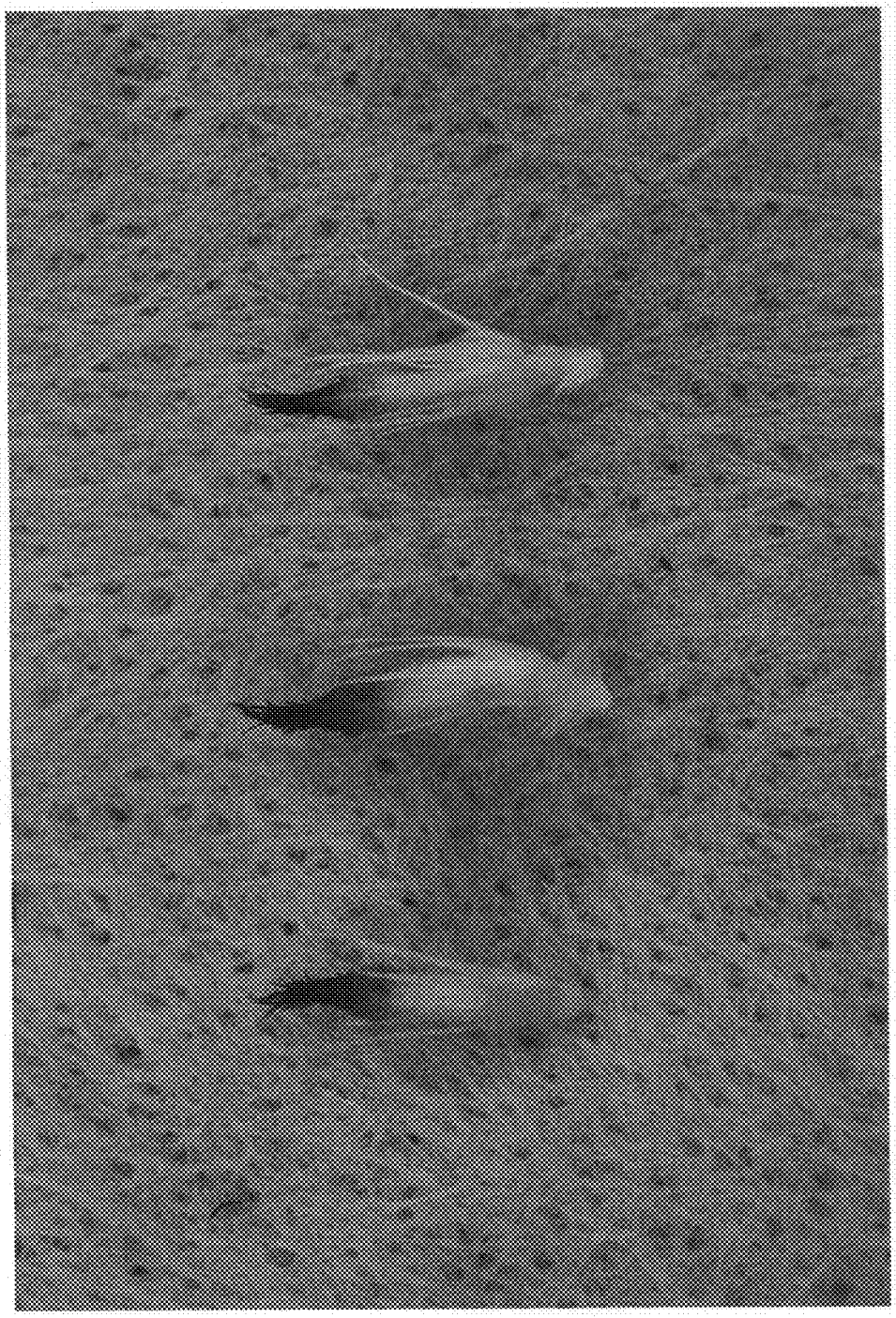
FIG. 1 is a photograph of the stamen of the new variety 'Georgia Sunset'.
Figure 2:
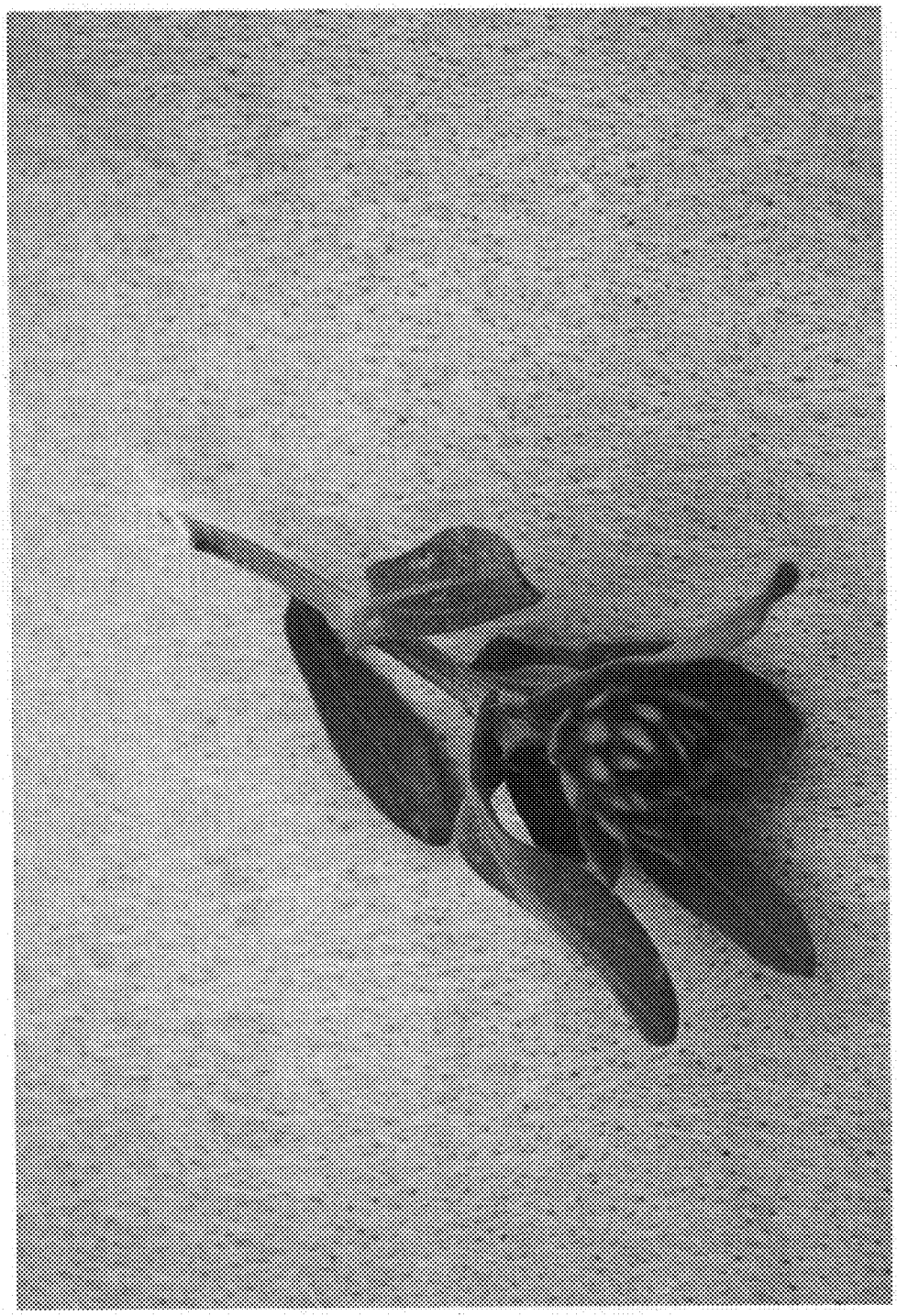
FIG. 2 is a photograph of the sepals and peduncle of the new variety 'Georgia Sunset'.
Figure 3:
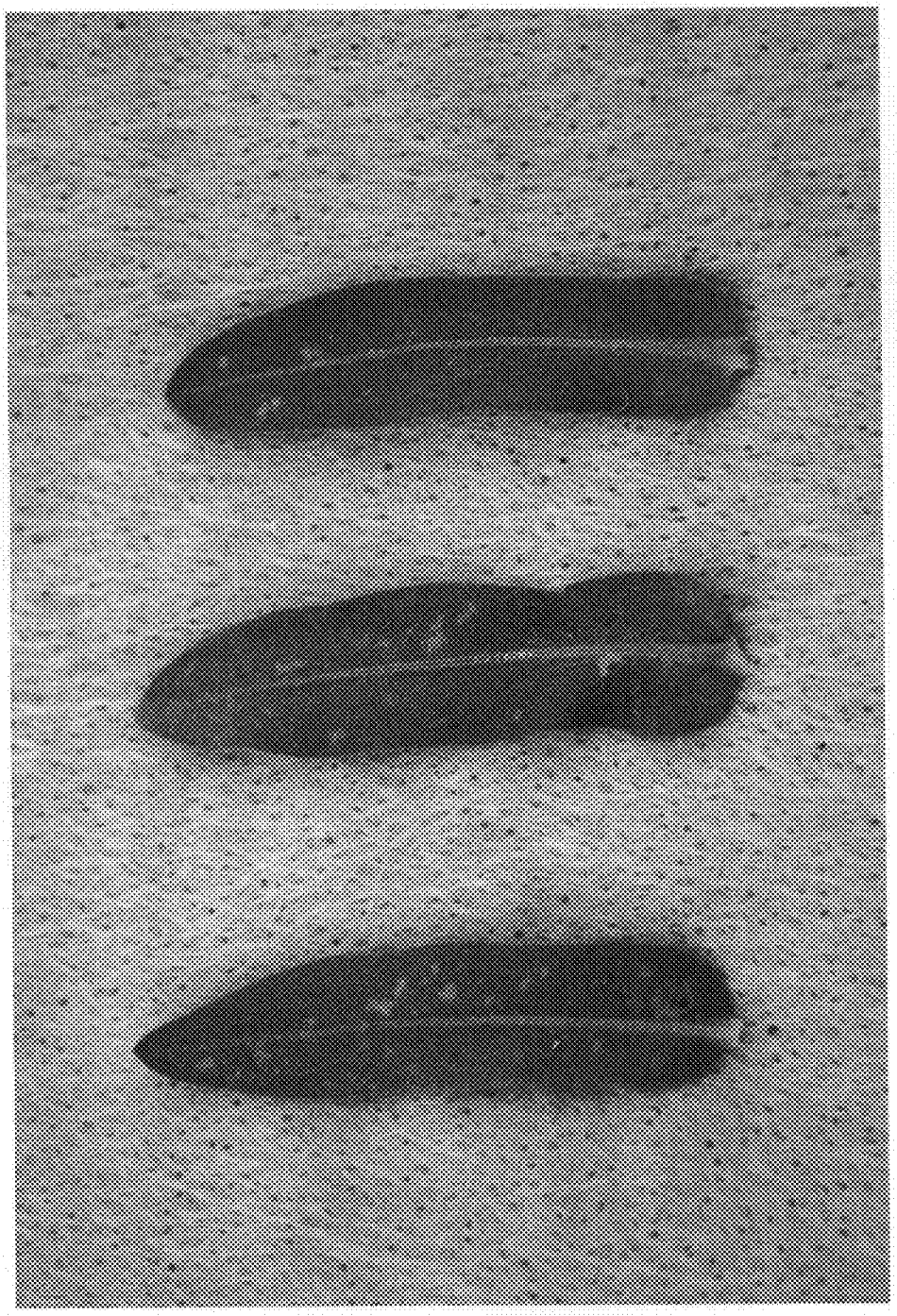
FIG. 3 is a photograph of the leaves of the new variety 'Georgia Sunset'.
Figure 4:
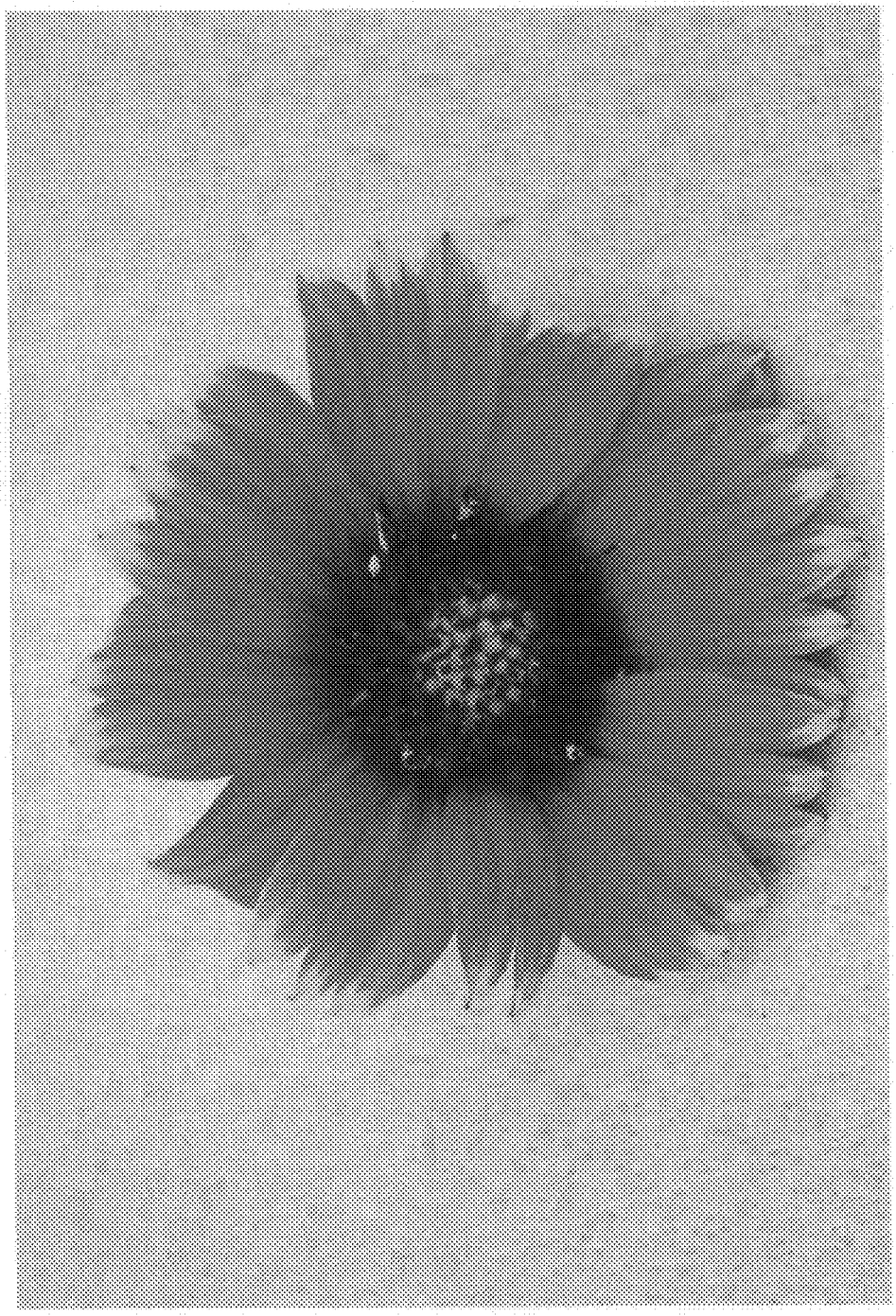
FIG. 4 is a photograph of the flower of the new variety 'Georgia Sunset'.
Figure 5:
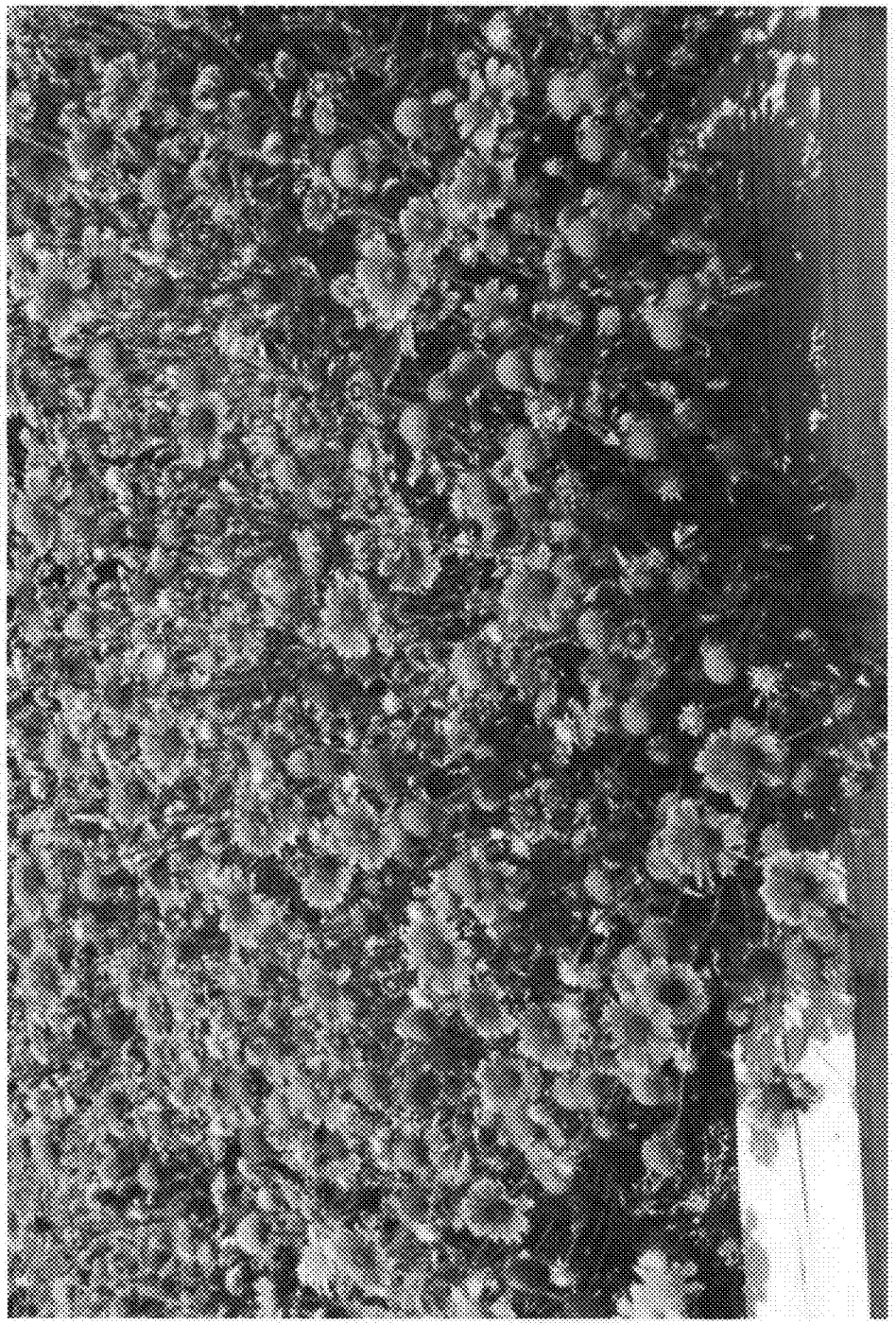
FIG. 5 is a photograph of plants of the new variety 'Georgia Sunset' in a garden setting.
Figure 6:
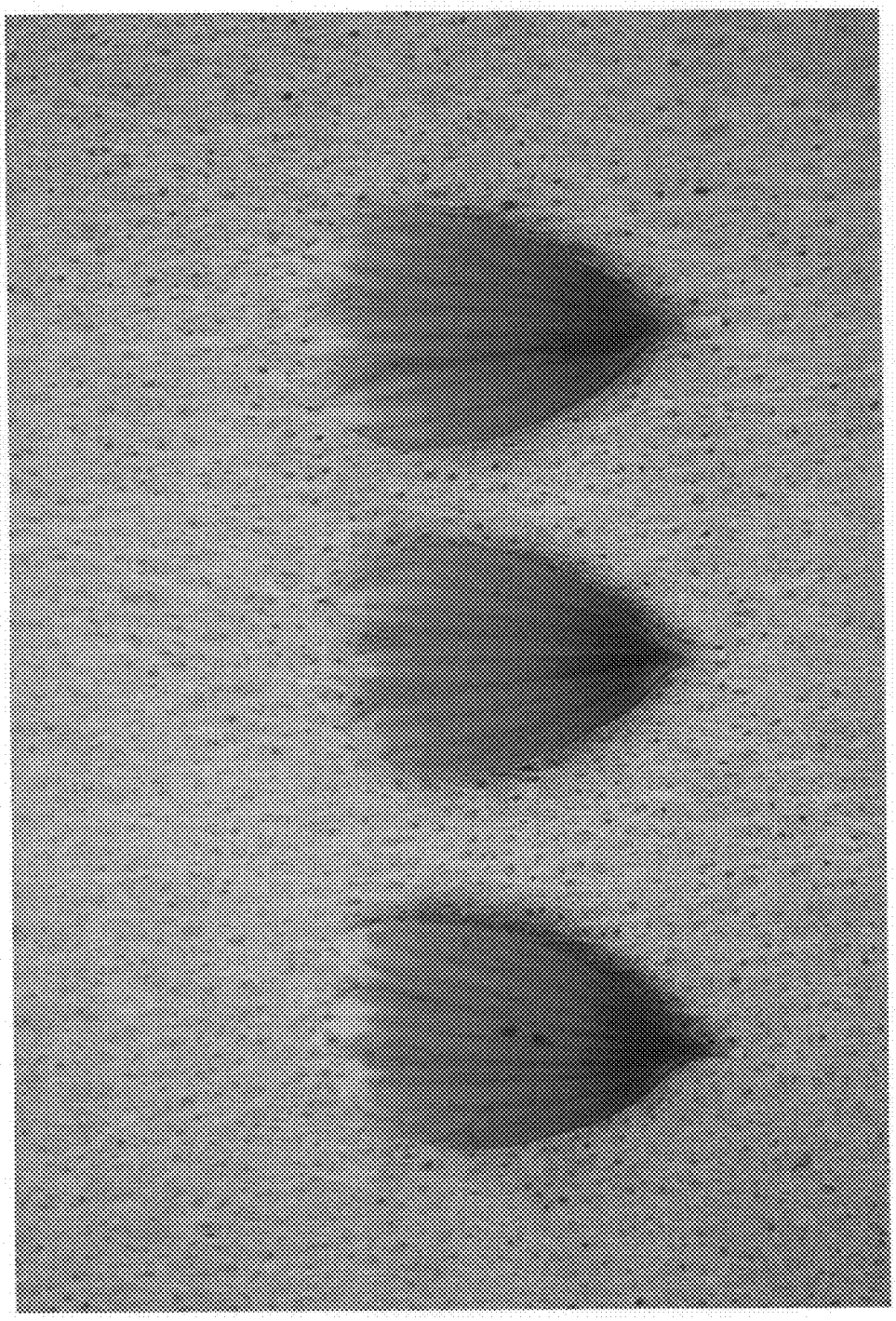
FIG. 6 is a photograph of the petals of the new variety 'Georgia Sunset'.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following is a detailed description of the botanical and pomological characteristics of the new variety 'Georgia Sunset'. Where dimensions, sizes, colors, and other characteristics are given, it is to be understood that such characteristics are approximations and averages set forth as accurately as practicable. The descriptions reported herein are largely from specimen plants grown in Watkinsville and Athens, Ga. Plants were about 1 to about 3 years old when evaluated.

PLANT

Habit: Mounding to round.
Size: Approximately 43.6 cm tall by about 3 years of age.
Texture: Medium.

STEM

Color: About Moderate yellow green RHS 147B.
Length: Approximately 36.4 cm.
Diameter: Approximately 0.2 cm.
Pubescence: Pilose.
Exfoliation: None.
Shape: Cylindrical with longitudinal ridges.
Odor: None.
Internode length: Approximately 1.6 cm.

FOLIAGE

Leaf color through seasons: About Dark green RHS 137A.
Length: Approximately 3.8 cm.
Width: Approximately 9 cm.
Apex: Acute.
Bases: Rounded.
Margin: Entire.
Shape: Elliptical.
*Lobes.*—N/A.
*Sinuses.*—N/A.
Vein color: About Green RHS 138A.
Pubescence: Pilose.
Leaf arrangement: Alternate.
Leaf venation: Single linear vein.
Texture:
*Thickness.*—Approximately <0.1 mm.
*Degree of waxiness.*—N/A.
Petioles: None.

FLOWER BUDS

Shape: Accrescent.
Pubescence: Pilose pubescence present on bracts.
Time of full maturity: Summer season.
Time range for showiness: Spring through summer season.

FLOWERS

Inflorescence:
*Type.*—Radiate head.
*Diameter.*—Approximately 6.6 cm.
Flower peduncle:
*Color.*—About Yellow-green RHS 144B.
*Pubescence.*—Pilose.
Flowers per inflorescence: Approximately >10.
Ray flowers:
*Color (from apex to base).*—About Red RHS 46A, Red RHS 45A, and Yellow RHS 15A all present.
*Length.*—Approximately 2.6 cm.
*Width.*—Approximately 1.6 cm.
*Apex.*—Lobed.
*Base.*—Attenuate.
*Margin.*—Entire.
*Pubescence.*—None.
Disc flowers:
*Color (from apex to base).*—About Red RHS 46B and Yellow-orange 16A all present.
*Length.*—Approximately 1 cm.
*Width.*—Approximately 0.2 mm.
Stamen:
*Length.*—Approximately 0.4 mm.
*Width.*—Approximately <0.1 mm.
*Color.*—About Yellow-orange RHS 16A.
*Pollen color.*—About Yellow-orange RHS 16A.
*Pubescence.*—None.
Pistil:
*Shape.*—Y-shaped.
*Length.*—Approximately 0.7 cm.
*Width.*—Approximately <0.1 cm.
*Position.*—Superior.
*Color.*—About Red RHS 53A.
*Pubescence.*—None.
Stigma:
*Shape.*—Linear.
*Color.*—About Red RHS 53A.
*Pubescence.*—None.
Style:
*Length.*—Approximately 0.6 cm.
*Shape.*—Linear.
*Color.*—About Red RHS 53A.
*Pubescence.*—None.
Ovary:
*Shape.*—Inferior, unilocular with 1 basal ovule.
*Number.*—Approximately 2.
*Pubescence.*—None.

Typical plants of the new variety 'Georgia Sunset' and similar *Gaillardia* varieties ('Sunburst Burgundy' and 'Sunburst Scarlet Halo') were measured and compared at the University of Georgia Trial Gardens at Athens, Ga. Seedlings of the new variety 'Georgia Sunset' that were selected in 2007 were established in the same year. In June 2007, propagules of the new variety 'Georgia Sunset' were grown in the greenhouse and replanted in the field in May 2008 for observation. In 2009, plants of the new variety 'Georgia Sunset' were planted at Athens, Ga. along with the *Gaillardia* varieties 'Sunburst Burgundy' and 'Sunburst Scarlet Halo'. Plant measurements for each of the varieties are provided in Table 1. The approximate averages of these properties are as follows:

TABLE 1

COMPARISON OF THE NEW VARIETY 'GEORGIA SUNSET' WITH OTHER *GAILLARDIA* PLANT VARIETIES AT ATHENS, GEORGIA

| Cultivar | Plant height (cm)[a] | Flower diameter (cm)[b] | Leaf length (cm)[b] | Leaf width (cm)[b] |
|---|---|---|---|---|
| 'Georgia Sunset' | 43.6 | 6.6 | 3.8 | 0.9 |
| 'Sunburst Burgundy' | 50.3 | 6.1 | 5.1 | 1.4 |
| 'Sunburst Scarlet Halo' | 48.6 | 6.3 | 7.8 | 1.5 |

| Cultivar | Flower color[c] | Leaf & stem colord[d] |
|---|---|---|
| 'Georgia Sunset' | ray: 46A, 45A, 15A<br>disc: 46B, 16A | leaf: 137A<br>stem: 138A |
| 'Sunburst Burgundy' | ray: 46B<br>disc: 46A | leaf; 138B<br>stem: 138B |
| 'Sunburst Scarlet Halo' | ray: 6A, 45B<br>disc: 46A | leaf: 136B<br>stem: 137A |

[a]Average of 10 measurements from soil to top of flower
[b]Average of 10 measurements
[c]RHS color chart, 2001. More than 1 color may occur on a ray or disc flower, RHS colors range from apex to base of flower
[d]Upper and lower sides of leaves have same RHS color

What is claimed is:

1. A new and distinct variety of *Gaillardia* plant named 'Georgia Sunset', substantially as illustrated and described herein.

* * * * *